(12) United States Patent
Vivancos Martinez et al.

(10) Patent No.: US 11,529,353 B2
(45) Date of Patent: Dec. 20, 2022

(54) PHARMACEUTICAL COMPOSITION COMPRISING PALBOCICLIB

(71) Applicant: Synthon B.V., Nijmegen (NL)

(72) Inventors: Marta Vivancos Martinez, Sant Boi de Llobregat (ES); Lisardo Alvarez Fernandez, Sant Boi de Llobregat (ES); Rohit Kumar, Sant Boi de Llobregat (ES); Jose Velada Calzada, Nijmegen (NL)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 16/633,339

(22) PCT Filed: Jul. 25, 2018

(86) PCT No.: PCT/EP2018/070227
§ 371 (c)(1),
(2) Date: Jan. 23, 2020

(87) PCT Pub. No.: WO2019/020715
PCT Pub. Date: Jan. 31, 2019

(65) Prior Publication Data
US 2020/0147089 A1 May 14, 2020

(30) Foreign Application Priority Data
Jul. 28, 2017 (EP) .................... 17183861

(51) Int. Cl.
*A61K 31/519* (2006.01)
*A61K 9/16* (2006.01)

(52) U.S. Cl.
CPC .......... *A61K 31/519* (2013.01); *A61K 9/1652* (2013.01)

(58) Field of Classification Search
None
See application file for complete search history.

(56) References Cited

U.S. PATENT DOCUMENTS

| | | | |
|---|---|---|---|
| 2008/0021037 A1* | 1/2008 | Beylin | A61P 37/06 514/252.16 |
| 2015/0368365 A1* | 12/2015 | Petermann | C08B 13/00 424/400 |
| 2018/0207100 A1* | 7/2018 | Ibrahim | A61K 31/519 |

FOREIGN PATENT DOCUMENTS

| | | |
|---|---|---|
| CN | 105213322 A | 1/2016 |
| WO | 03/062236 A1 | 7/2003 |
| WO | 2005/005426 A1 | 1/2005 |
| WO | 2014/128588 A1 | 8/2014 |
| WO | 2016/024249 A1 | 2/2016 |
| WO | 2016/030439 A1 | 3/2016 |
| WO | 2016/156070 A1 | 10/2016 |
| WO | 2016/193860 A1 | 12/2016 |
| WO | 2017/145054 A1 | 8/2017 |
| WO | 2018/073574 A1 | 4/2018 |

* cited by examiner

*Primary Examiner* — David J Blanchard
*Assistant Examiner* — Daniel F Coughlin
(74) *Attorney, Agent, or Firm* — Buscher Patent PLLC

(57) ABSTRACT

The present invention relates to a pharmaceutical granulate composition comprising Palbociclib free base, having improved bioavailability.

20 Claims, 4 Drawing Sheets

Form A XRPD

PHARMACEUTICAL COMPOSITION COMPRISING PALBOCICLIB

BACKGROUND OF THE PRESENT INVENTION

The present invention relates to a pharmaceutical composition, particularly a granulate composition comprising Palbociclib free base, having improved bioavailability.

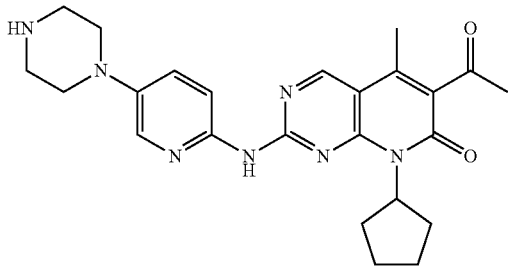 [SMILES: CC(=O)c1c(C)c2cnc(Nc3ccc(N4CCNCC4)cn3)nc2n(C2CCCC2)c1=O]

Palbociclib, having the chemical structure shown above, is a selective inhibitor of the cyclin-dependent kinases CDK4 and CDK6. It is indicated for the treatment of breast cancer. Palbociclib free base and pharmaceutically acceptable salts thereof are disclosed in WO2003062236.

A Palbociclib containing immediate release capsule is approved under the brand name Ibrance® (Pfizer) in the EU and US. Generally, the marketed Palbociclib capsules comprise 75, 100 or 150 mg of Palbociclib.

WO 2005/005426 describes the preparation of Palbociclib free base and various mono- and di-acid addition salts thereof including various polymorphic forms of the isethionate salt. According to WO2014128588, Palbociclib obtained from a standard salt break process was found to be highly static and found to form large hard agglomerates that were not dispersed at sieving and could not be used in the development. According to the applicant, when Palbociclib free base having a larger primary particle size and a surface area of ≤2 $m^2/g$ is used, the manufacture and physiochemical properties are improved.

Palbociclib free base has a pH dependent solubility. At or below pH 4, Palbociclib behaves as a high-solubility compound in water. Above pH 4, the solubility of the drug substance reduces significantly.

WO2016156070 describes that when Palbociclib free base with a surface area ranging from 2.1 to 6.0 $m^2/g$ as determined by BET-nitrogen adsorption analysis is used, a powder that allows straight forward pharmaceutical processing and has a high dissolution rate is obtained.

WO2016156070 describes that the needle shape primary particles are not preferred because they are not so easy to handle as compared with the flake like or plate like primary particles. Due to the solubility problems that Palbociclib presents, it will be even more advantageous to use crystalline Palbociclib free base with a surface area higher than 6 $m^2/g$.

The objective of the present invention is to provide a formulation with Palbociclib having a high surface area to improve its solubility but that still allows straight forward pharmaceutical processing.

BRIEF DESCRIPTION OF THE PRESENT INVENTION

The present invention relates to a pharmaceutical granulate composition comprising a therapeutically effective dose of crystalline Palbociclib and one or more pharmaceutically acceptable excipients, wherein the Palbociclib crystals are needles with a surface area between 6 and 10 $m^2/g$, and a particle size distribution d(0.9) between 5 and 50 micrometers.

It also provides a granulate suitable for making such a pharmaceutical composition and a process for making such a pharmaceutical composition.

DETAILED DESCRIPTION OF THE PRESENT INVENTION

The present invention relates to a pharmaceutical granulate composition comprising a therapeutically effective dose of crystalline Palbociclib and one or more pharmaceutically acceptable excipients, wherein the Palbociclib crystals are needles with a surface area between 6 and 15 $m^2/g$, and a particle size distribution d(0.9) between 5 and 50 micrometers.

The prior art reports manufacturing problems when Palbociclib with a higher surface area is used, especially if it has the shape of needles.

It was surprisingly found that when Palbociclib having a high surface area and crystalline needle shape is used with a particle size distribution d(0.9) between 5 and 50 micrometers and when manufactured as a granulate, the problems described in the prior art are solved.

A pharmaceutical granulate composition is defined as a pharmaceutical composition manufactured by a granulation process.

A high surface area is defined as a surface area≥6 $m^2/g$, preferably between 6 and 15 $m^2/g$, more preferably between 6 and 10 $m^2/g$, even more preferably between 6 and 8 $m^2/g$ as determined by BET-nitrogen adsorption analysis.

The present invention relates to a pharmaceutical granulate composition of Palbociclib having a particle size distribution d(0.9) from 5 to 50 micrometers, preferably from 7 to 40, micrometers, more preferably from 10 to 30 micrometers even more preferably from 7 to 30 micrometers. Each value of the lower limit of such range can be combined with any value of the upper limit of such range that is not inconsistent with it. It is established and well understood in the field of particle size measurement that particle size and/or particle size distribution cannot be directly related to the specific surface area of particles, since any assumption about the particle shape and as such specific surface area fails to account for specific surface texture and/or specific surface contours and/or specific surface defects and/or localized surface properties of the particles, any and all of which can have an influence on specific surface area and associated properties. The surface properties and in particular specific surface area can be strongly affected, for example, by the high energy input associated with mechanical grinding processes for the reduction of particle size. For example, the high energy input can cause a disruption of the crystal lattice on the particle surface and the creation of crystal defects can result in an increased specific surface area when compared to particles having a similar particle size distribution but obtained by a controlled crystallization process.

Figure 1:
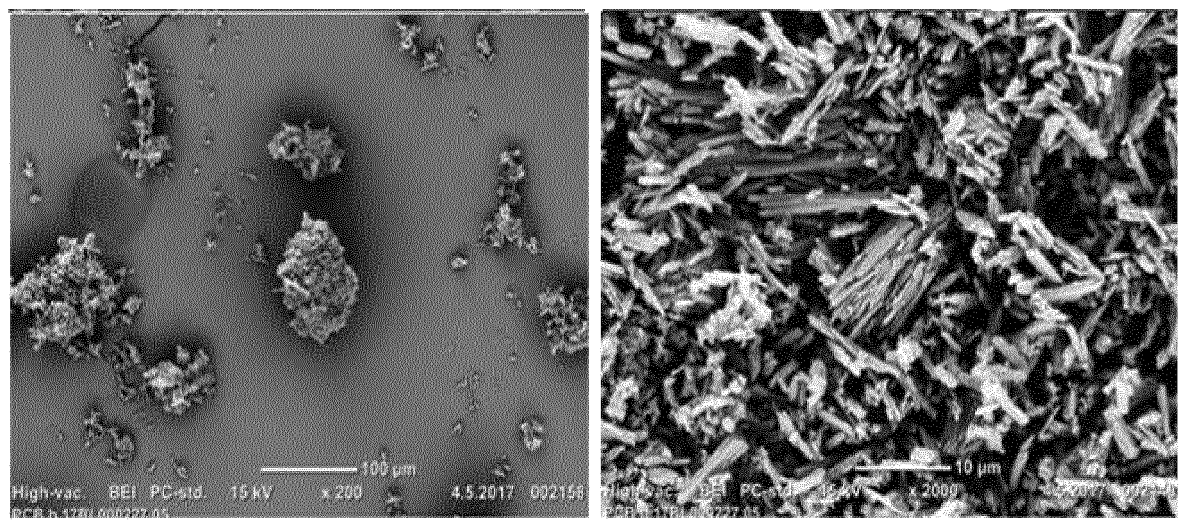
FIG. 1: Electron microscopic images of the Palbociclib material obtained from example 1.

In a preferred embodiment the crystalline Palbocicb of the present invention has the needle shaped crystals as agglomerates. A characteristic electron microscopic image of the agglomerates is displayed in FIG. 1.

A needle shaped crystal of Palbociclib refers to acicular, highly elongated crystal having similar width and breadth.

An agglomerate is defined as an assembly of tightly bound crystals of Palbociclib. Preferably, the crystalline Palbociclib of the present invention is characterized as being a free base polymorph Form A, having a characteristic powder X-ray diffraction pattern (XRPD) comprising reflections at 2-Theta angles of 5.0±0.2, 7.9±0.2, 10.0±0.2, 11.5±0.2, 22.5±0.2. A typical XRPD of free base polymorph Form A is displayed in FIG. 2. The corresponding data is tabulated in table 1

TABLE 1

| Angle 2-Theta ° ± 0.2 | d value Angstrom | Intensity % % |
|---|---|---|
| 5.03 | 17.56 | 37.8 |
| 7.95 | 11.11 | 25.7 |
| 10.07 | 8.78 | 75.7 |
| 11.49 | 7.69 | 53.6 |
| 14.01 | 6.32 | 17.3 |
| 15.08 | 5.87 | 11.6 |
| 15.93 | 5.56 | 22.2 |
| 17.07 | 5.19 | 61.0 |
| 17.46 | 5.08 | 15.8 |
| 18.67 | 4.75 | 39.6 |
| 19.66 | 4.51 | 54.8 |
| 20.15 | 4.40 | 19.8 |
| 21.11 | 4.21 | 21.8 |
| 21.86 | 4.06 | 16.7 |
| 22.45 | 3.96 | 100.0 |
| 22.97 | 3.87 | 36.6 |
| 23.69 | 3.75 | 13.5 |
| 28.51 | 3.13 | 16.5 |
| 28.83 | 3.09 | 13.0 |
| 30.15 | 2.96 | 12.0 |

The Palbociclib of the present invention has a high surface area and a small particle size. These characteristics may result in formulations with a high solubility which may not be bioequivalent to the marketed product. This problem can be solved by the addition of one or more dissolution modulating agents to the composition.

The dissolution modulating agents according to this invention are pharmaceutically acceptable excipients capable to modulate the drug dissolution rate in acidic conditions, particularly at pH 2.

The dissolution modulating agents of this invention are:
Disintegrants which may be added to the pharmaceutical granulate composition to promote the breakup of the tablet or capsule into smaller fragments in an aqueous environment, thereby increasing the available surface area and promoting a more rapid release of the active pharmaceutical ingredient. In order to slow down the dissolution profile the amount of disintegrant used in the composition is from 2 to 4%, more preferably from 2.5 to 3.5%, even more preferably 3% by weight based on the total weight of the composition. Suitable examples of disintegrants to be used in accordance with the present invention include crospovidone, sodium starch glycolate, croscarmellose sodium, and mixtures of any of the foregoing. A preferred disintegrant is sodium starch glycolate. Disintegrants can be added as an intragranular or extragranular excipient. Disintegration occurs by rapid uptake of water followed by rapid and enormous swelling. When added as intragranular excipient it helps to break the granules whereas when added as extragranular excipient it helps the tablet or capsule to disintegrate. In a preferred embodiment of the present invention the disintegrant is added extragranularly and intragranularly. In a more preferred embodiment, 40-70% of the total weight of the disintegrant in the composition is added intragranularly and 30-60% extragranularly. Even more preferably, 50-60% of the total weight of disintegrant in the composition is added intragranularly and 40-50% extragranularly.

Binders hold the excipients that are present in a tablet or capsule together. Binders ensure that tablets, capsules and granules can be formed having the desired or required mechanical strength. Binders which are suitable for use in accordance with the present invention include co-povidone, povidone, hydroxypropyl methylcellulose, hydroxy propylcellulose, and sodium carboxyl methylcellulose. Preferred binders are binders having a viscosity of 250 mPa·s or less for a 10% aqueous solution at 25° C., even more preferred are binders having a viscosity of 250 mPa·s or less for a 10% aqueous solution at 25° C. Most preferred binder is co-povidone. Binders are preferably used in an amount of from 3-10% by weight based on the total weight of the composition, more preferably in an amount form 4-8%, and most preferably in an amount from 6-8%.

A combination of one or more binders and one or more disintegrants.

Besides binders and disintegrants, the one or more pharmaceutically acceptable excipients to be used in accordance with the present invention can be chosen from, for example, diluents, lubricants, and glidants.

Diluents are fillers which are used to increase the bulk volume of the pharmaceutical granulate composition. Generally, by combining a diluent with the active pharmaceutical ingredient, the final product is given adequate weight and size to assist in production and handling. Suitable examples of diluents to be used in accordance with the present invention include starch, pregelatinized starch, microcrystalline cellulose, calcium phosphate, lactose, sorbitol, mannitol and sucrose. In a preferred embodiment of the present invention, microcrystalline cellulose and/or lactose are used as diluents.

In a preferred embodiment the formulation contains arginine hydrochloride, which acts as formic acid scavenger reducing impurities caused by the Maillard reaction resulting from the interaction between Palbociclib with the reducing sugars contained in the excipients.

The pharmaceutical granulate composition of the invention preferably comprises:
a) at least one diluent in an amount of from 40% to 80% by weight based on the total weight of the composition;
b) at least one binder in an amount of from 3% to 10% by weight based on the total weight of the composition;
c) at least one disintegrant in an amount of from 2 to 4% by weight based on the total weight of the composition.

The pharmaceutical granulate composition of the invention may also contain a lubricant. Lubricants are generally used in order to reduce sliding friction. In particular, to decrease friction at the interface between a tablet or capsule's surface. Suitable lubricants to be used in accordance with the present invention include magnesium stearate, calcium stearate, stearic acid, glyceryl behenate, hydrogenated vegetable oil, and glycerine fumarate.

The pharmaceutical granulate composition of the invention may also contain a glidant. Glidants enhance product flow by reducing interparticulate friction. A suitable example is colloidal silicon dioxide.

Lubricants and glidants preferably are used in a total amount of from 0.05% to 5% by weight based on the total weight of the composition.

In a preferred embodiment, the pharmaceutical granulate composition of the present invention contains the following ingredients, based on the total weight of the composition:
a. A therapeutically effective dose of Palbociclib wherein the Palbociclib crystals are needles with a surface area between 6 and 15 m$^2$/g, and a particle size distribution d(0.9) between 5 and 50 micrometers, in an amount of from 25% to 35% by weight;
b. Microcrystalline cellulose or pregelatinized starch or a mixture thereof in an amount of from 30% to 50% by weight;
c. Lactose in an amount of from 10% to 30% by weight;
d. Sodium starch glycolate in an amount of from 2% to 4% by weight;
e. Copovidone in an amount of from 3% to 10% by weight; and
f. A lubricant and a glidant in an amount of from 0.05% to 5% by weight.

In one embodiment of the present invention, the therapeutically effective dose of Palbociclib is 75 mg, 100 mg or 125 mg.

The pharmaceutically acceptable excipients to be used in accordance with the present invention, can be used intragranularly, extragranularly, or both.

The pharmaceutical compositions described herein can be made using conventional methods and equipment well-known in the art.

The pharmaceutically composition of the present invention can be prepared by wet or dry granulation. Dry granulation is preferred.

The present invention further relates to a pharmaceutical granulate composition as described hereinabove, prepared by a dry-granulation process, which process comprises:
1. Mixing Palbociclib, wherein the Palbociclib crystals are needles with a surface area between 6 and 15 m$^2$/g, and a particle size distribution d(0.9) between 5 and 50 micrometers, and one or more pharmaceutically acceptable excipients to form a mixture, optionally adding a dissolution modulating agent such as a disintegrant in an amount of from 2% to 4% by weight based on the total weight of the composition, a binder or a combination of both;
2. Dry-granulating the resulting mixture;
3. Milling the mixture through a mesh size from 1 to 3 mm;
4. Further mixing the obtained granulate with one or more further pharmaceutically acceptable excipients to form a further mixture;
5. Lubricating the blend;
6. Optionally encapsulating the blend.

The present invention still further relates to a granulate suitable for making a pharmaceutical granulate composition as described hereinabove, prepared by a dry-granulation process, which process comprises:
1. Mixing Palbociclib, wherein the Palbociclib crystals are needles with a surface area between 6 and 15 m$^2$/g, and a particle size distribution d(0.9) between 5 and 50, and one or more pharmaceutically acceptable excipients to form a mixture, preferably using a dissolution modulating agent such as a disintegrant in an amount of from 2% to 4% by weight based on the total weight of the composition, a binder or a combination of both;
2. Dry-granulating the resulting mixture.

The particle size distribution (PSD) of the granules obtained after the dry granulation process and milling may have an impact on the dissolution profile. Certain amount of coarse granules is required to decrease the dissolution rate. Different milling processes might be used, for instance hammer impact mill (such as Fitz-mill) or rotating impeller mill (such as BTS). Hammer mill is preferred from manufacturing point of view because it results in a more efficient process. A mesh size between 1 and 3 mm is used. Preferably, a mesh size of 2 mm is used. The mesh can have screen openings with or without a rasping surface.

More than 30% of the total amount of granules of the present invention, preferably from 35 to 50%, have a particle size distribution (PSD)>250 μm. PSD (%)>250 μm is defined as the percentage of the total amount of granules that has been retained in a 250 μm mesh.

The pharmaceutical granulate compositions of the present invention can be formulated as a capsule or tablet. Capsules are preferred.

The pharmaceutical composition of the present invention is preferably packaged in blister pack material. Particularly preferred blister pack material to be used in accordance with the present invention is cold forming blister packs. Cold forming blister packs, also known as aluminum/aluminum blister packs, adopt cold forming aluminum film and lidding material of aluminum foil. The use of aluminum offers a nearly complete barrier for moisture, allowing an extended product expiration date. In this way the possible Maillard reaction is prevented. The pharmaceutical composition of the present invention is stable. After storage for 6 months at 40° C./75% RH, the total amount of impurities is still low.

The pharmaceutical composition in accordance with the present invention may be used as a medicament. The pharmaceutical composition typically may be used in the treatment of breast cancer.

The present invention is illustrated by the following Examples.

EXAMPLES

The particle size distribution of the blend is measured by mechanical agitation (dry sieving method) based on Ph.Eur.monograph 2.9.38. Each test sieve (from 45 to 710 μm) is tared and test sample is placed on the top (coarsest) sieve. The nest of sieves is agitated for 10 minutes by using the Restch AS 200 Digit analytical sieve equipment. Finally, each sieve is reweighted in order to determine the mass of material retained on each one and in the collecting pan.

SEM was Performed under Standard Conditions.

Figure 2:
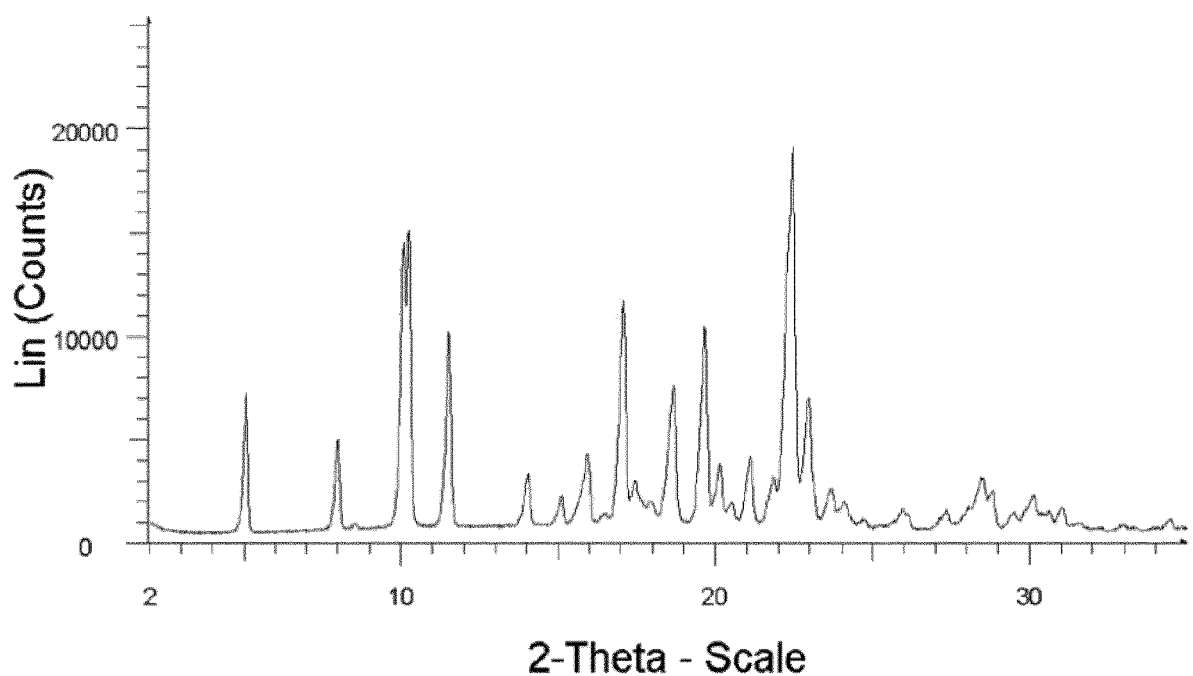
FIG. 2: XRPD of Palbociclib Form A

The full powder X-Ray Diffraction (XRPD) of FIG. 2 was measured using Bruker-AXS D8 Vario diffractometer with θ/2θ geometry (reflection mode), equipped with a Lynxeye detectorand applying the following measurement conditions:
Start angle (2θ): 2.0°
End angle (2θ): 35.0°
Scan step width: 0.02°
Scan step time: between 0.2-2.0 seconds
Radiation type: Cu
Radiation wavelengths: 1.5406 Å (Kα1), primary monochromator used
Exit slit: 6.0 mm Focus slit: 0.2 mm Divergence slit: Variable (V20)

The particle size distribution (PSD) is determined with LASER diffraction analyzer Malvern Mastersizer 2000 which operates in size ranges from 0.02 μm to 2,000 μm. The wet dispersion is prepared from dry powder sample and added to the dispersion unit. Gained raw data are computed by software to PSD with the use of Mie theory. This method is based on Ph. Eur. Method 2.9.31 and USP <429>.

The specific surface area (SSA) is assessed with a Quantachrome NOVA touch 2LX. The $N_2$ is used as measuring gas and BET method is used to evaluate SSA. The following setup has been used for the measurement:

Adsorbate: Nitrogen

Sample cell: 9 mm large bulb cell, long; Measurement is performed with the corresponding filler rod Sample masses*: approximately ¾ of cell bulb Degassing conditions: 960 min at 30° C. under vacuum (ramping 10° C./min)

Measured points of isotherm: 11 equidistant points in the range 0.05-0.30 $p/p_0$**

Points analyzed using BET: 7equidistant points from whole range 0.05-0.20 $p/p_0$ Use data reduction adsorbate model: Yes ($N_2$)

Bath thermal delay: at least 600 s $P_0$ Option: continuous (measured each 30 minutes)

Void volume mode: Helium measure

Equilibration time: 160 s

Equilibration timeout: 2400 s

Tolerance: 0.05

* Used amount of sample depends on its SSA and other physical parameters. The real surface area of sample in measuring cell should be between 1 $m^2/g$ and 20 $m^2/g$.
** Points above or below this range can be measured.

EXAMPLE 1

Preparation Palbociclib Free Base 3.4 kg of Palbociclib was mixed with 3.68 kg of water to form a suspension. The mixture was mixed with 17 kg of water and to the mixture 0.86 kg of HCl (35-39%, w/w) was added. The mixture was heated at 40° C., Palbociclib was dissolved and pH of the solution was adjusted with HCl to be between 3 and 4. Afterwards, the Palbociclib.HCl solution was filtered.

A NaOH aqueous solution was prepared with 0.37 kg of NaOH dissolved in 5 kg of water. This solution was added to the solution of Palbociclib.HCl, during 60-80 min until final pH 11-12.5. Yellow solid of Palbociclib free base precipitated from the mixture.

Isolated solid was isolated by filtration and washed with 9,1 kg of water and 2.5 kg of acetone. The obtained solid was dried on the filter for at least 12 hours. The solid was then dried at room temperature for at least 10 hours. The solid was milled over a sieve with 0.8 mm mesh. The milled product was dried at 28-30° C. for at least 4 hours.

Palbociclib with surface area 6.9 $m^2/g$, a needle morphology and D90 11.5 μm was obtained.

EXAMPLE 2

Palbociclib Formulation 125 mg

| Component | 125 mg | % |
|---|---|---|
| Palbociclib (SBL) | 125,000 | 27.78% |
| Microcrystalline cellulose (Vivapur 102) | 95,917 | 41.3% |
| Lactose monohydrate (Supertab 11SD) | 70,458 | 15.66% |
| Sodium starch glycolate (Glycolis) | 6,750 | 3% |
| Co-PVP (Plasdone s-630) | 36,000 | 8.00% |
| Colloidal Silicon Dioxide (Aerosil 200VV Pharma) | 10,125 | 2.3% |
| Magnesium stearate (Ligamed MF-2-V) | 4,500 | 2.00% |

EXAMPLE 3

Figure 4:
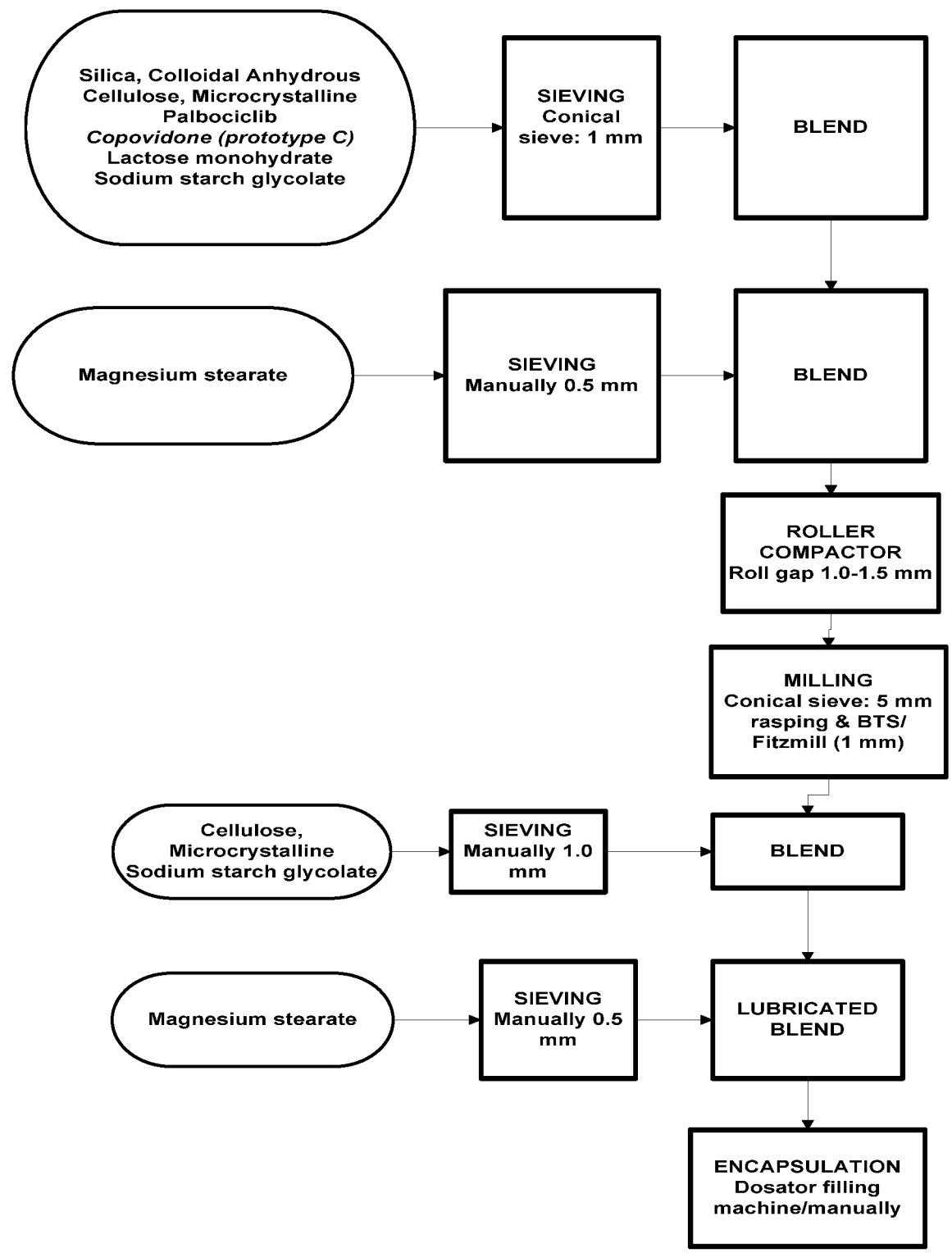
FIG. 4: A flowchart showing a process to manufacture pharmaceutical compositions of the invention.

Process to Manufacture Pharmaceutical Compositions According to the Present Invention is Shown in FIG. 4

EXAMPLE 4

Comparison of Pharmaceutical Granulate Composition of the Present Envention with Ibrance®

Figure 3:
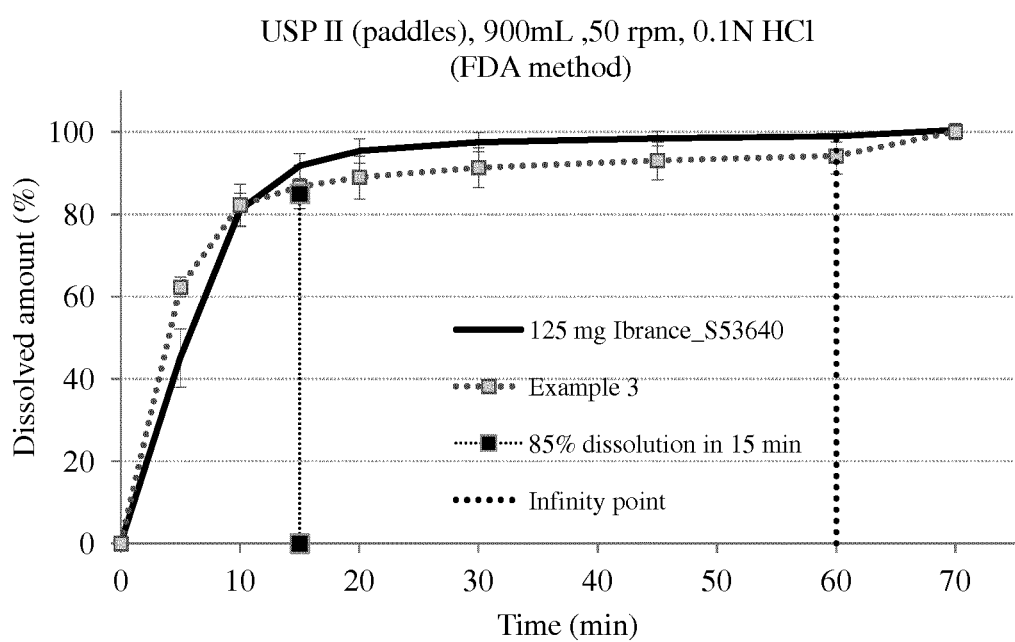
FIG. 3: Comparison of pharmaceutical granulate composition of the present invention with Ibrance®

The formulation resulting from Example 3 is bioequivalent to the commercial product Ibrance®, when measured at 900 ml HCl 0.1N using an USP apparatus II at 50 rpm as shown in FIG. 3.

The invention claimed is:

1. A pharmaceutical granulate composition comprising a therapeutically effective dose of crystalline Palbociclib free base and one or more pharmaceutically acceptable excipients, wherein the Palbociclib crystals are needles with a surface area between 6 and 15 $m^2/g$, and a particle size distribution d(0.9) between 5 and 50 micrometers; and wherein said crystalline Palbociclib is polymorph Form A.

2. The pharmaceutical granulate composition according to claim 1 having one or more dissolution modulating agents.

3. The pharmaceutical granulate composition according to claim 2 wherein the one or more dissolution modulating agents is (i) a disintegrant in an amount of from 2% to 4% by weight based on the total weight of the composition, (ii) a binder, or (iii) a combination of both.

4. The pharmaceutical granulate composition according to claim 3 wherein the disintegrant is added intragranularly and extragranularly.

5. The pharmaceutical granulate composition according to claim 3 wherein the disintegrant is sodium starch glycolate.

6. The pharmaceutical granulate composition according to claim 3 wherein the binder has a viscosity of 250 mPas or less for a 10% aqueous solution at 25° C.

7. The pharmaceutical granulate composition according to claim 6 wherein the binder is co-povidone or hydroxypropyl methylcellulose.

8. The pharmaceutical granulate composition according to claim 3 wherein the amount of binder ranges from 3-10% by weight based on the total weight of the composition.

9. The pharmaceutical granulate composition according to claim 1 wherein the composition further comprises 40 to 80% diluents by weight based on the total weight of the composition.

10. The pharmaceutical granulate composition according to claim 1 comprising, based on the total weight of the composition:
a) a therapeutically effective dose of Palbociclib in an amount of from 25% to 35% by weight;
b) microcrystalline cellulose or pregelatinized starch or a mixture thereof in an amount of from 30% to 50% by weight;
c) lactose in an amount of from 12% to 30% by weight;
d) sodium starch glycolate in an amount of from 2 to 4% by weight;
e) copovidone in an amount of from 3% to 10% by weight; and
f) lubricant and a glidant in an amount of from 0.05% to 5% by weight.

11. A granulate according to claim 1 prepared by a dry granulation process, which process comprises
a) mixing crystalline Palbociclib Form A, wherein the Palbociclib crystals are needles with a surface area between 6 and 15 m$^2$/g, and a particle size distribution d(0.9) between 5 and 50 micrometers, and one or more pharmaceutically acceptable excipients to form a mixture, and
b) dry-granulating the resulting mixture.

12. The granulate according to claim 11 wherein the granules particle size distribution PSD >250 µm is from 35 to 50%.

13. The granulate according to claim 12 wherein the granule size is obtained via hammer impact mill.

14. A pharmaceutical granulate composition according to claim 1 prepared by a dry-granulation process, which process comprises a) mixing crystalline Palbociclib Form A having needle-like primary particles with a surface area between 6 and 15 m$^2$/g, and a particle size distribution d(0.9) between 5 and 50 micrometers and one or more pharmaceutically acceptable excipients to form a mixture;
b) dry-granulating the resulting mixture;
c) milling the mixture to form a granulate;
d) further mixing the obtained granulate with one or more further pharmaceutically acceptable excipients to form a further mixture blend;
e) lubricating the blend; and
f) optionally encapsulating the blend.

15. A pharmaceutical composition comprising the granulate according to claim 1 in a capsule.

16. The pharmaceutical granulate composition according to claim 2 wherein said one or more dissolution modulating agents comprises sodium starch glycolate.

17. The pharmaceutical granulate composition according to claim 14 wherein said milling obtains a granulate that passes through a mesh size from 1 mm to 3 mm.

18. The pharmaceutical granulate composition according to claim 14 wherein said milling is carried out with a hammer impact mill.

19. The pharmaceutical composition according to claim 14, wherein said one or more pharmaceutically acceptable excipients mixed with said Palbociclib comprise a diluent, a binder, and a disintegrant; and said further pharmaceutically acceptable excipients that are mixed with said granulate comprise a diluent and a disintegrant.

20. The pharmaceutical composition according to claim 19, wherein said excipients contained within said granulate comprise microcrystalline cellulose, copovidone, and sodium starch glycolate; and said excipients contained extra-granular comprise microcrystalline cellulose, sodium starch glycolate, and said lubricant.

* * * * *